(12) United States Patent
Hermes et al.

(10) Patent No.: US 10,159,525 B2
(45) Date of Patent: Dec. 25, 2018

(54) ELECTROSURGICAL END EFFECTORS

(71) Applicant: Covidien LP, Mansfield, MA (US)

(72) Inventors: Paul Hermes, Guilford, CT (US);
Daniel Wallace, Santa Cruz, CA (US)

(73) Assignee: Covidien LP, Mansfield, MA (US)

( * ) Notice: Subject to any disclaimer, the term of this patent is extended or adjusted under 35 U.S.C. 154(b) by 259 days.

(21) Appl. No.: 15/104,766

(22) PCT Filed: Nov. 3, 2014

(86) PCT No.: PCT/US2014/063653
§ 371 (c)(1),
(2) Date: Jun. 15, 2016

(87) PCT Pub. No.: WO2015/094493
PCT Pub. Date: Jun. 25, 2015

(65) Prior Publication Data
US 2016/0317216 A1 Nov. 3, 2016

Related U.S. Application Data

(60) Provisional application No. 61/917,591, filed on Dec. 18, 2013.

(51) Int. Cl.
*A61B 18/14* (2006.01)
*A61B 34/30* (2016.01)
(Continued)

(52) U.S. Cl.
CPC ...... *A61B 18/1445* (2013.01); *A61B 18/1206* (2013.01); *A61B 18/16* (2013.01);
(Continued)

(58) Field of Classification Search
CPC ............ A61B 18/1442; A61B 18/1445; A61B 18/1447; A61B 2018/1442;
(Continued)

(56) References Cited

U.S. PATENT DOCUMENTS

| | | |
|---|---|---|
| 5,080,660 A | 1/1992 | Buelna |
| 6,030,384 A | 2/2000 | Nezhat |

(Continued)

FOREIGN PATENT DOCUMENTS

| | | |
|---|---|---|
| DE | 102007017966 B3 | 11/2008 |
| JP | 2002513623 A | 5/2002 |

(Continued)

OTHER PUBLICATIONS

Extended European Search Report issued in European Application No. 14870749.0 dated Sep. 20, 2017.
(Continued)

*Primary Examiner* — Jaymi Della

(57) ABSTRACT

Bipolar electrosurgical forceps for use with a robotic surgical system. Electrodes on a first grasping jaw member align with corresponding electrodes on a second jaw member, allowing localized energy to seal tissue between the first and second jaw members. The first jaw member has an open centerline slot, exposing the tissue in the slot. The exposed tissue enables a second, similar forceps to be used with an opposing arm to treat the tissue in the slot. In embodiments, the precise motion of the robotic arms supporting the first and second forceps guides a distal tip electrode of the second forceps precisely within the open centerline slot of the first forceps to treat tissue. In this manner, the complex assemblies and control systems associated with moving blades of conventional electrosurgical forceps are eliminated.

2 Claims, 16 Drawing Sheets

(51) Int. Cl.
*A61B 34/37* (2016.01)
*A61B 18/16* (2006.01)
*A61B 18/12* (2006.01)
*A61B 18/00* (2006.01)
*A61B 34/32* (2016.01)

(52) U.S. Cl.
CPC ............ *A61B 34/30* (2016.02); *A61B 34/37* (2016.02); *A61B 34/32* (2016.02); *A61B 2018/0063* (2013.01); *A61B 2018/00601* (2013.01); *A61B 2018/126* (2013.01); *A61B 2018/1467* (2013.01); *A61B 2018/162* (2013.01); *A61B 2018/165* (2013.01); *A61B 2034/305* (2016.02)

(58) Field of Classification Search
CPC ...... A61B 2018/145; A61B 2018/1452; A61B 2018/1455; A61B 2018/146; A61B 2018/1462
See application file for complete search history.

(56) References Cited

U.S. PATENT DOCUMENTS

| | | | |
|---|---|---|---|
| 6,152,923 A | 11/2000 | Ryan | |
| 6,223,100 B1 | 4/2001 | Green | |
| 6,309,397 B1 | 10/2001 | Julian et al. | |
| 6,491,691 B1 | 12/2002 | Morley et al. | |
| 6,500,176 B1 | 12/2002 | Truckai et al. | |
| 6,840,938 B1 | 1/2005 | Morley et al. | |
| 6,905,497 B2 | 6/2005 | Truckai et al. | |
| 6,953,461 B2 | 10/2005 | McClurken et al. | |
| 6,994,708 B2 | 2/2006 | Manzo | |
| 7,125,403 B2 | 10/2006 | Julian et al. | |
| 7,367,973 B2 | 5/2008 | Manzo et al. | |
| 7,422,592 B2 | 9/2008 | Morley et al. | |
| 7,493,191 B1 | 2/2009 | Miller | |
| 7,946,800 B2 | 5/2011 | Hosek et al. | |
| 8,182,476 B2 | 5/2012 | Julian et al. | |
| 8,224,484 B2 | 7/2012 | Swarup et al. | |
| 8,423,182 B2 | 4/2013 | Robinson et al. | |
| 8,452,447 B2 | 5/2013 | Nixon | |
| 8,504,201 B2 | 8/2013 | Moll et al. | |
| 8,551,116 B2 | 10/2013 | Julian et al. | |
| 2001/0014801 A1* | 8/2001 | Tovey | A61B 17/0469 606/1 |
| 2002/0107517 A1* | 8/2002 | Witt | A61B 18/1442 606/50 |
| 2005/0096502 A1 | 5/2005 | Khalili | |
| 2005/0171533 A1 | 8/2005 | Latterell et al. | |
| 2006/0020272 A1 | 1/2006 | Gildenberg | |
| 2006/0052779 A1* | 3/2006 | Hammill | A61B 18/1442 606/51 |
| 2008/0119870 A1* | 5/2008 | Williams | A61B 34/71 606/130 |
| 2010/0106297 A1 | 4/2010 | Inazumi et al. | |
| 2010/0217436 A1 | 8/2010 | Jones et al. | |
| 2011/0028964 A1* | 2/2011 | Edwards | A61B 18/1442 606/33 |
| 2011/0071670 A1 | 3/2011 | Mankame et al. | |
| 2011/0098854 A1 | 4/2011 | Tarragona et al. | |
| 2011/0295422 A1 | 12/2011 | Hasenzahl | |
| 2012/0116416 A1 | 5/2012 | Neff et al. | |
| 2012/0191243 A1 | 7/2012 | Haas et al. | |
| 2012/0215220 A1 | 8/2012 | Manzo et al. | |
| 2012/0253344 A1* | 10/2012 | Dumbauld | A61B 18/1445 606/52 |
| 2013/0024024 A1 | 1/2013 | Namiki | |
| 2013/0144116 A1 | 6/2013 | Cooper et al. | |

FOREIGN PATENT DOCUMENTS

JP 2004089591 A 3/2004
WO WO-2010-017266 2/2010

OTHER PUBLICATIONS

International Search Report for (PCT/US2014/063653) date of completion is Feb. 3, 2015 (7 pages).
Chinese Office Action issued in corresponding Chinese Application No. 201480069428X dated Aug. 28, 2017.
Japanese Office Action issued in corresponding Japanese Appln. No. 2016-539078 dated Aug. 7, 2018, together with English language translation (15 pages).

* cited by examiner

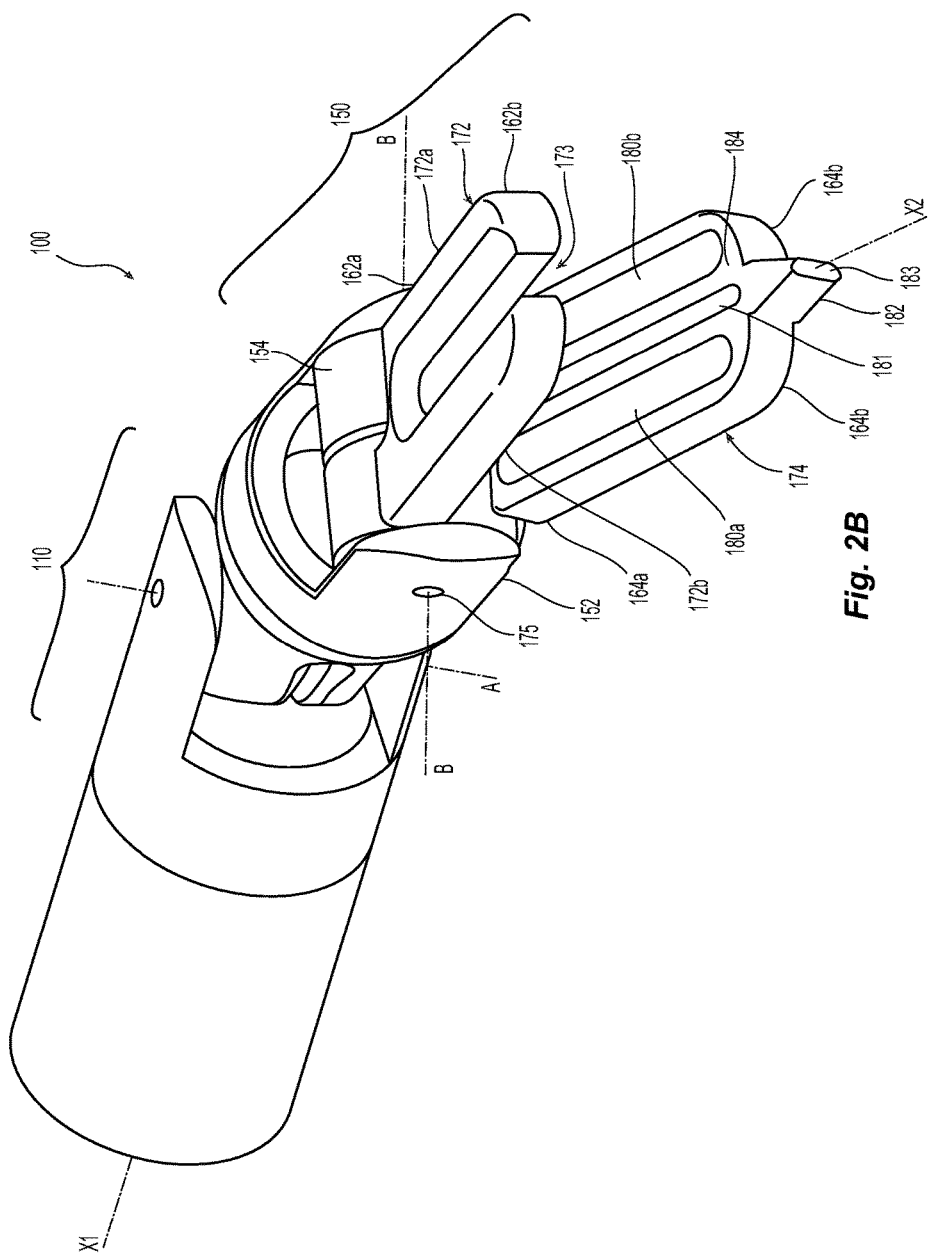

ELECTROSURGICAL END EFFECTORS

CROSS-REFERENCE TO RELATED APPLICATIONS

This application is a U.S. National Stage Application filed under 35 U.S.C. § 371(a) of International Patent Application No. PCT/US2014/063653, filed Nov. 3, 2014, which claims the benefit to U.S. Provisional Patent Application No. 61/917,591, filed Dec. 18, 2013, the entire disclosure of each of which is incorporated by reference herein.

BACKGROUND

1. Technical Field

The present disclosure relates to surgical instruments, and more specifically, to improved electrosurgical jaw assemblies for use with robotic surgical systems.

2. Background of Related Art

Electrosurgery uses alternating current electrical signals to cut or coagulate biologic tissue endogenically. Electrosurgery techniques have been used in robotic surgery by passing these electrical signals through electrodes in end effectors attached to the ends of robotic arms. In some instances, two different types of end effectors are used. A first end effector type includes an active electrode, and a second end effector type includes a return electrode to which current passing through the patient's body from the active electrode flows. Having two different end effector types adds cost and complexity due to the need to obtain and install both end effector types on different arms corresponding to a user preferred orientation, such as a preferred left-right orientation of the active and return electrodes on the arms, in order to perform some types of electrosurgery.

These two types of end effectors are also used in some instances exclusively for electrosurgery. If a user needed to perform another function, such as grasping, the user would have to switch end effectors. Such switching of end effectors during surgery lengthens surgical procedure times and increases costs, because separate grasping and electrosurgical end effectors must be obtained and interchanged.

A single end effector that eliminates the need for different active and return electrode end effectors in electrosurgical applications, and which reduces the need to switch end effectors during surgery, would be a welcome advance.

SUMMARY

The dexterity of robotic surgical systems allows for arrangements of multiple instruments that allow for a level of functionality that might be challenging in a single instrument. According to one aspect of the present disclosure, a pair of grasper-like bipolar instruments is presented which, in combination with each other, can be mated to perform an array of bipolar tasks. These tasks include, without limitation, bipolar cutting, bipolar vessel sealing, and hemostasis of small vessels using bipolar coagulation.

According to another aspect of the present disclosure, a first robotic arm includes a first bipolar grasping forceps having a first bipolar grasping jaw member with two distinct electrodes embedded within an insulative material. The electrodes on the first grasping jaw member align with corresponding electrodes (e.g., ground or return electrodes) on a second jaw member, allowing localized energy to seal tissue between the first and second jaw members. The first jaw member has a centrally-disposed slot defined therein where energy will not pass to the second jaw member during the tissue sealing process, thus allowing the tissue in the slot to remain unsealed or untreated. After the tissue is sealed, a second, similar bipolar grasping forceps may be used in a second, opposing robotic arm to treat (e.g., cut, seal, etc.) the tissue in the slot.

In one embodiment, the disclosed bipolar forceps has an insulated protrusion with a small electrode at the distal tip. Because the area of the tip electrode is small, current density is relatively high, allowing the tip energy to cut the tissue in the slot as the energy conducts from the tip to a contact pad (electrode) on the jaw member opposite of the slot. Electrodes in the jaw member are configured to enable sealing energy to be conducted between the outer sealing pads of the first forceps, and cutting energy to be conducted between the protruding tip electrode of the second forceps and the central cutting electrode of the first forceps to perform a "two-handed" sealing and/or cutting operation. Advantageously, the high-precision motion of the robotic arms supporting the first and second forceps facilitate the operation by guiding the distal tip electrode of the second forceps precisely within the open centrally-disposed slot of the first forceps.

In another embodiment, the disclosed bipolar forceps may additionally or alternatively include an insulated longitudinal ridge on the reverse side of the second jaw member having a uninsulated top surface. The ridge is configured to fit within the open centrally-disposed slot of the first jaw member of another bipolar forceps to perform electrosurgical sealing and/or cutting operations.

In some embodiments, the cutting procedure is performed at least in part by a preprogrammed set of instructions executable on a processor operatively coupled to the forceps, generator, and/or robotic arms which choreographs the cutting and/or sealing motion between the two forceps.

In yet another embodiment, the disclosed bipolar forceps may additionally or alternatively include a cutting blade positioned within a base of the centrally-disposed slot providing protection for the blade and configured to facilitate cutting sutures when a suture is pulled into the slot.

Advantageously, the design of a bipolar sealing instrument in accordance with the present disclosure is greatly simplified, because the complex assemblies and control systems associated with moving blades of conventional electrosurgical forceps are eliminated, which, in turn, reduces costs, enhances reliability, and may improve patient outcomes. In addition, a single device type could be used to easily ligate and cut tissue, allowing procedures to move quickly without the interruptions associated with changing instruments frequently. This further reduces costs by decreasing the number of instruments used, reducing consumables, and lowering disposal and sterilization costs.

In another aspect of the present disclosure, a method of providing cooperative or two-handed sealing and cutting includes connecting opposite first and second forceps with opposite polarities, e.g., the right hand slot grip seals against the right hand base grip and the left hand base grip cuts against the right hand base grip. Alternatives may include providing a single conductive pad on the un-slotted jaw member or positioning the cutting protrusion on the outer edge of the second jaw member.

The present disclosure relates to an electrosurgical end effector for use with a robot arm of a robotic surgical system. In one embodiment, the end effector includes a wrist assembly and a jaw assembly. The wrist assembly includes a proximal hub defining a longitudinal axis, and a distal hub pivotally connected to the proximal hub. The proximal hub and the distal hub are pivotable about a first pivot axis that is oriented transverse to the longitudinal axis of the proximal hub.

The jaw assembly includes first and second jaw members pivotally connected to the distal hub of the wrist assembly. The first jaw member includes a housing, and a longitudinal slot defined in the housing of the first jaw member. The longitudinal slot forms first and second grasping members, where each grasping member includes a grasping surface configured to face an opposing grasping surface of the second jaw member. The first jaw member includes a first sealing electrode disposed on the first grasping surface, and a second sealing electrode disposed on the second grasping surface.

The second jaw member includes a housing, and a grasping surface that is configured to face the grasping surface of the first jaw member. The second jaw member includes first and second return electrodes longitudinally disposed on the grasping surface, where the first and second return electrodes are configured to oppose the corresponding first and second sealing electrodes of the first jaw member. The second jaw member includes a third return electrode longitudinally disposed on the grasping surface located centrally between first and second return electrodes, where the third return electrode is configured to oppose the longitudinal slot of the first jaw member. At least one of the housing and the grasping surface of the first and/or second jaw member may be formed from ceramic material.

In some embodiments, the electrosurgical end effector includes a cutting electrode assembly having a support ridge disposed longitudinally on the top portion of the housing of the second jaw member, and a longitudinal electrode is positioned along the top of the support ridge. The cutting electrode assembly may be configured to be operably received within the longitudinal slot. In some embodiments, the cutting electrode assembly is movable between a first (raised) position where the longitudinal electrode is positioned above the top portion of the housing of the second jaw member, and a second (lowered) position where the longitudinal electrode is positioned closer to, or flush with, the top portion of the housing of the second jaw member.

In yet other embodiments, the electrosurgical end effector includes a tip electrode assembly having a tip electrode support extending distally from a distal portion of the housing of the second jaw member, and a tip electrode disposed on a distal tip of the tip electrode support. The tip electrode assembly may be configured to be operably received within the longitudinal slot. In some embodiments, the tip electrode assembly is movable between a first (raised) position where the tip electrode is positioned above the surface of a distal portion of the housing of the second jaw member, and a second (lowered) position where the tip electrode is positioned closer to, or flush with, the surface of a distal portion of the housing of the second jaw member.

In still other embodiments, at least one of the first sealing electrode, second sealing electrode, first return electrode, second return electrode, and third return electrode may be flush with grasping surface and/or may be disposed upon the grasping surface. The first sealing electrode, second sealing electrode, first return electrode, second return electrode, and third return electrode may be configured for independent electrical communication with an electrosurgical generator.

In another aspect of the present disclosure, a robotic surgical system for performing electrosurgical procedures is described. In an example embodiment, the system includes an end effector operably coupled to a robot arm. The end effector includes a first jaw member having a housing and a longitudinal slot defined in the housing which forms first and second grasping members. Each grasping member has a grasping surface configured to face an opposing grasping surface of a second jaw member. The first jaw member includes a first sealing electrode disposed on the first grasping surface, and a second sealing electrode disposed on the second grasping surface. The end effector includes a second jaw member having a housing, and a grasping surface included in the housing that is configured to face the grasping surface of the first jaw member. The second jaw member includes first and second return electrodes longitudinally disposed on the grasping surface which are configured to oppose corresponding first and second sealing electrodes of the first jaw member. The second jaw member includes a third return electrode longitudinally disposed on the grasping surface located centrally between the first and second return electrodes. The third return electrode is configured to oppose the longitudinal slot of the first jaw member.

The example system includes a control device configured to manipulate at least one of the robot arm and the end effector according to a user input, and an electrosurgical generator in operable communication with the control device and the end effector. The generator is configured to selectively deliver electrosurgical energy to at least one of the first sealing electrode, second sealing electrode, first return electrode, second return electrode, and third return electrode. In some embodiments, the system includes a second end effector operably coupled to a second robot arm.

The control device may be configured to manipulate at least one of the robot arm and at least one of the end effectors according to a preprogrammed sequence of actions. In some embodiments, the preprogrammed sequence of actions includes introducing the cutting electrode assembly of the first end effector into the longitudinal slot of the second end effector to grasp tissue therebetween, delivering electrosurgical energy between the cutting electrode assembly of the first end effector and the return electrode of the second end effector to treat the tissue grasped therebetween, withdrawing the cutting electrode assembly of the first end effector from the longitudinal slot of the second end effector.

In embodiments, the preprogrammed sequence of actions may include introducing the tip electrode assembly of the first end effector into a first end of the longitudinal slot of the second end effector, delivering electrosurgical energy between the cutting electrode assembly of the first end effector and the third return electrode of the second end effector to treat tissue grasped between the first and second jaw members of the second end effector and exposed within the longitudinal slot thereof, moving the tip electrode assembly of the first end effector along the longitudinal slot of the second end effector toward a second end thereof to treat the exposed tissue, and withdrawing the tip electrode assembly of the first end effector from the longitudinal slot of the second end effector.

In embodiments, the preprogrammed sequence of actions may include delivering electrosurgical energy between at least one of the first sealing electrode and the first return electrode, and/or the second sealing electrode and the second return electrode.

In another aspect of the present disclosure, a method of performing electrosurgery is presented. The method includes positioning tissue between a cutting electrode of a first end effector associated with a first robotic arm and a return electrode of a second end effector associated with a second robotic arm. The cutting electrode is moved toward the return electrode to grasp the tissue therebetween. Electrosurgical energy is delivered between the cutting electrode and the return electrode to treat the tissue grasped therebetween, and the cutting electrode is withdrawn from the return electrode, which releases the treated tissue.

In some embodiments, the method may include grasping the tissue between at least one of a first sealing electrode and a first return electrode of the first end effector and/or at least one of a second sealing electrode and a first return electrode of the first end effector, and delivering electrosurgical energy between at least one of the first sealing electrode and the first return electrode of the first end effector, and/or the second sealing electrode and the second return electrode of the first end effector.

In yet other embodiments, the method may include moving the cutting electrode longitudinally along the return electrode to treat the tissue therebetween.

BRIEF DESCRIPTION OF THE DRAWINGS

Further details and aspects of example embodiments in accordance with the present disclosure are described in more detail below with reference to the appended Figures, wherein:

FIG. 2B is a top, perspective view of the end effector of FIG. 2A illustrating the jaw assembly in an open condition;

DETAILED DESCRIPTION OF EMBODIMENTS

Figure 1:
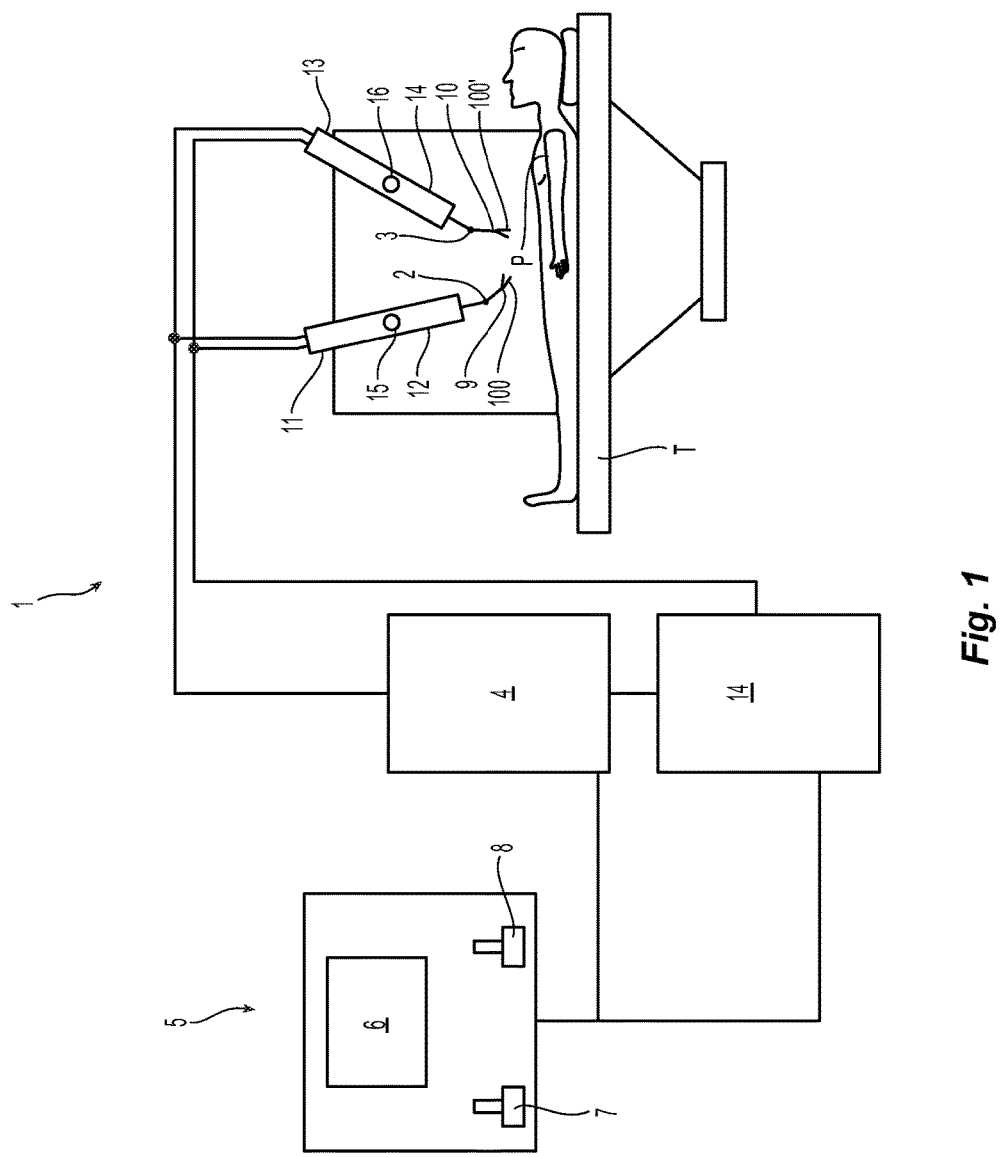
FIG. 1 is a schematic illustration of a medical workstation and operating console in accordance with the present disclosure.

Particular embodiments of the present disclosure are described hereinbelow with reference to the accompanying drawings; however, it is to be understood that the disclosed embodiments are merely examples of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. In the drawings and in the descriptions that follow, the term "proximal," as is traditional, shall refer to the end of the instrument that is closer to the user, while the term "distal" shall refer to the end that is farther from the user. In addition, as used herein in the description and in the claims, terms referencing orientation, e.g., "top", "bottom", "upper", "lower", "left", "right", and the like, are used with reference to the figures and features shown and described herein. It is to be understood that embodiments in accordance with the present disclosure may be practiced in any orientation without limitation. In this description, as well as in the drawings, like-referenced numbers represent elements which may perform the same, similar, or equivalent functions.

Referring initially to FIG. 1, a medical workstation is shown as workstation 1 and generally includes a plurality of robot arms 2 and 3, a control device 4, and an operating console 5 coupled with the control device 4. Operating console 5 includes a display device 6, which is configured to display three-dimensional images of the surgical site, and manual input devices 7, 8, which allow a person (not shown), for example a surgeon, to telemanipulate robot arms 2, 3 and instruments attached thereto.

Each of the robot arms 2, 3 includes a plurality of articulating members 11, 12 and 13, 14, respectively, which are connected by joints 15, 16 and are configured to facilitate the telemanipulation of robot arms 2, 3 with respect to patient P. Attaching devices 9 and 10 are disposed at distal ends of arms 2, 3 and are each configured to support an end effector 100, 100' (see FIG. 5A).

Robot arms 2, 3 may be driven by electric drives (not shown) that are connected to control device 4. Control device 4 (e.g., a computer) is configured to activate the drives by means of a computer program associated therewith in such a way that robot arms 2, 3, their attaching devices 9, 10 and respective end effectors 100, 100' execute a desired movement, which may be performed according to a movement defined by user inputs to manual input devices 7, 8 and, additionally or alternatively, movements defined by one or more algorithms associated with the computer program of control device 4. Control device 4 may also be configured in such a way that it regulates the movement of robot arms 2, 3 and/or of the electric drives.

Medical workstation 1 is configured for use on a patient P lying on a patient table T to be treated in a minimally invasive manner by means of end effector 100. Medical workstation 1 may also include more than two robot arms 2, 3, the additional robot arms likewise being connected to control device 4 and being telemanipulable by means of operating console 5 and otherwise similarly to robot arms 2, 3. A medical instrument (e.g., end effector 100) may also be attached to the additional robot arm(s).

Medical workstation 1 includes an electrosurgical generator 14 that is configured to receive inputs from operating console 5 and/or control device 4 and selectively deliver monopolar and/or bipolar electrosurgical energy to end effector(s) 100, 100' of robot arms 2, 3.

Reference may be made to U.S. Patent Publication No. 2012/0116416, filed on Nov. 3, 2011, entitled "Medical Workstation," the entire contents of which are incorporated herein by reference, for a detailed discussion of the construction and operation of the medical workstation 1.

Figure 2A:
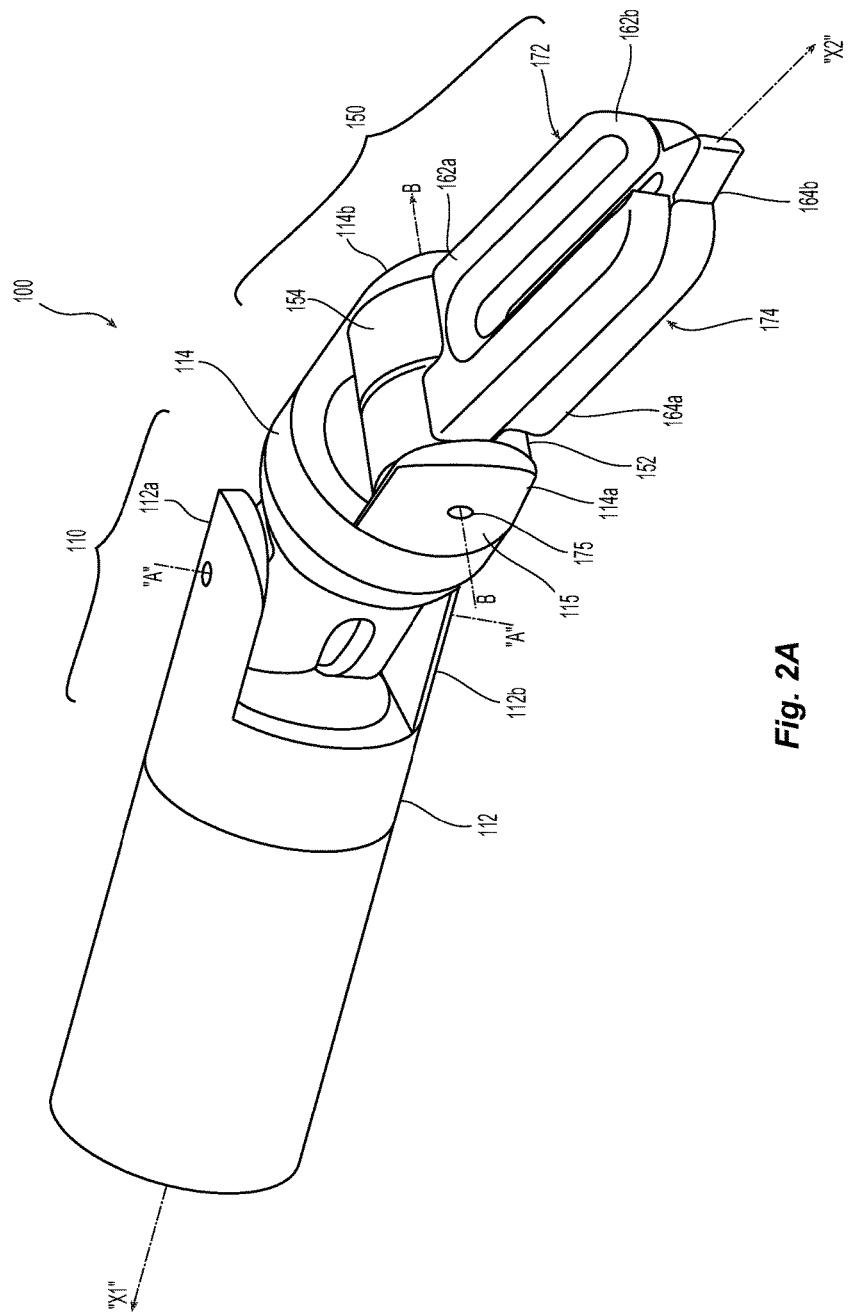
FIG. 2A is a top, perspective view of an end effector according to an embodiment of the present disclosure, for use in the medical workstation of FIG. 1, illustrating a jaw assembly thereof in a closed condition.
Figure 2C:
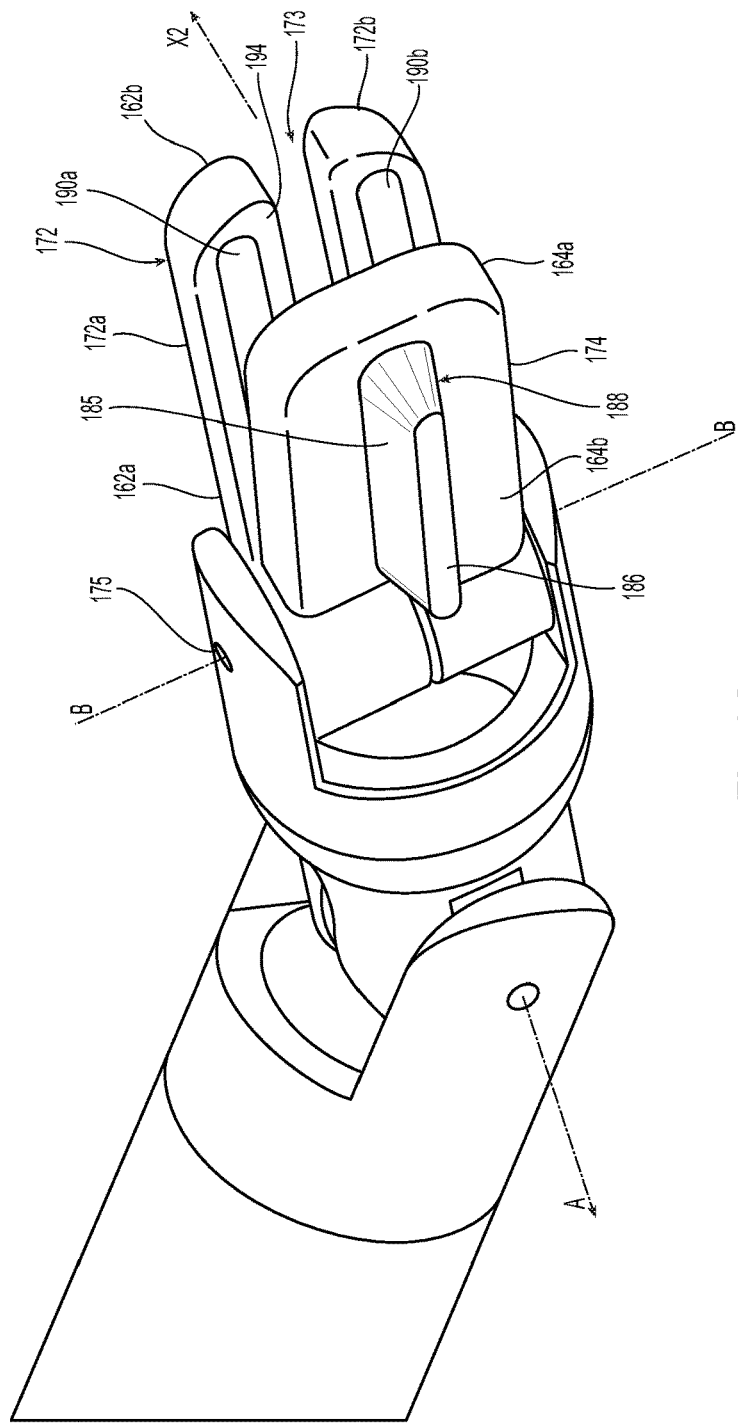
FIG. 2C is a bottom, perspective view of the end effector of FIG. 2A illustrating a cutting electrode disposed on a lower jaw member thereof.

Turning now to FIGS. 2A-2C, end effector 100 connects to robot arms 2, 3 and is manipulatable by control device 4 and includes a wrist assembly 110, and a jaw assembly 150 pivotally connected to the wrist assembly 110. Wrist assembly 110 includes a proximal hub 112, in the form of a distally extending clevis, defining a first longitudinal axis "X1." Proximal hub 112 defines a first pivot axis "A" that is oriented orthogonally to the first longitudinal axis "X1." In an embodiment, first pivot axis "A" may extend through the first longitudinal axis "X1." Proximal hub 112 includes a pair of spaced-apart, opposed uprights 112a, 112b that align along first pivot axis "A".

Wrist assembly 110 further includes a distal hub 114 pivotally connected to uprights 112a, 112b of proximal hub 112. Distal hub 114 includes a distally extending clevis 115 configured to define a second longitudinal axis "X2." Distal hub 114 defines a second pivot axis "B" that is oriented orthogonally to the first pivot axis "A" and orthogonally to the first longitudinal axis "X1." In an embodiment, when the first longitudinal axis "X1" is parallel with the second longitudinal axis "X2" (i.e., end effector 100 is in an axially aligned orientation), second pivot axis "B" may extend through first longitudinal axis "X1." Distal hub 114 includes a pair of spaced apart, opposed uprights 114a, 114b that align along second pivot axis "B".

Jaw assembly 150 includes a pair of jaw members 172, 174 separately and independently connected to corresponding support bases 152, 154. As best seen in FIGS. 3C and 4C, each jaw member 172, 174 includes a pivot point 161, 162 about which each jaw member 172, 174 pivots. Pivot points 161, 162 are spaced in axial alignment to define a common jaw pivot axis coincident with pivot axis "B" of distal hub 114. Each jaw member 172, 174 includes a respective proximal end 162a, 164a and a respective distal end 162b, 164b. A pin 175 or the like pivotally connects each pivot point 161, 162 of respective jaw member 172, 174 to distal hub 114 to enable jaw member 172, 174 to move between a first (open) position as illustrated in FIG. 2B and a second (closed) position as illustrated in FIG. 2A.

Figure 3A:
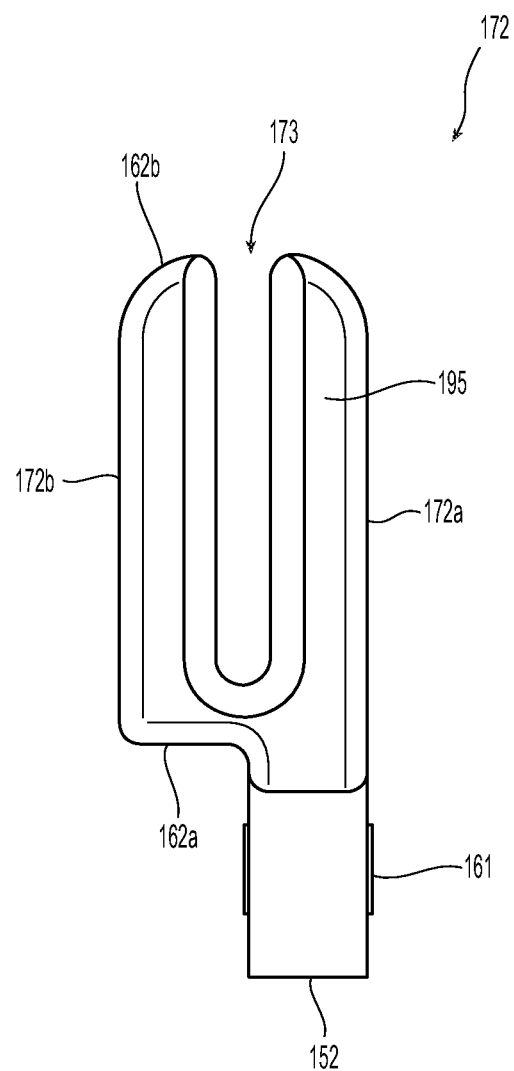
FIG. 3A is a view of a non-grasping side of an upper jaw member in accordance with the present disclosure.
Figure 3B:
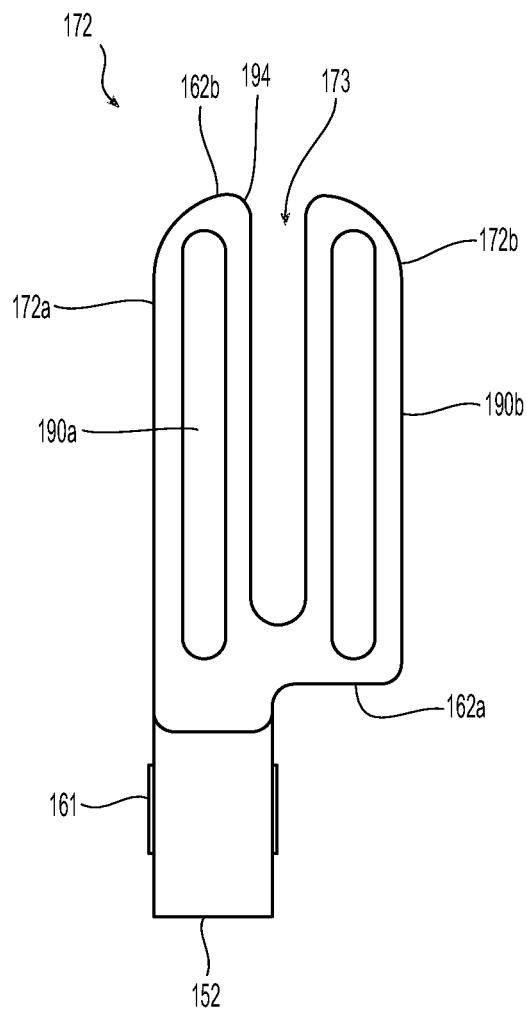
FIG. 3B is a view of a grasping side of the upper jaw member in accordance with the present disclosure.
Figure 3C:
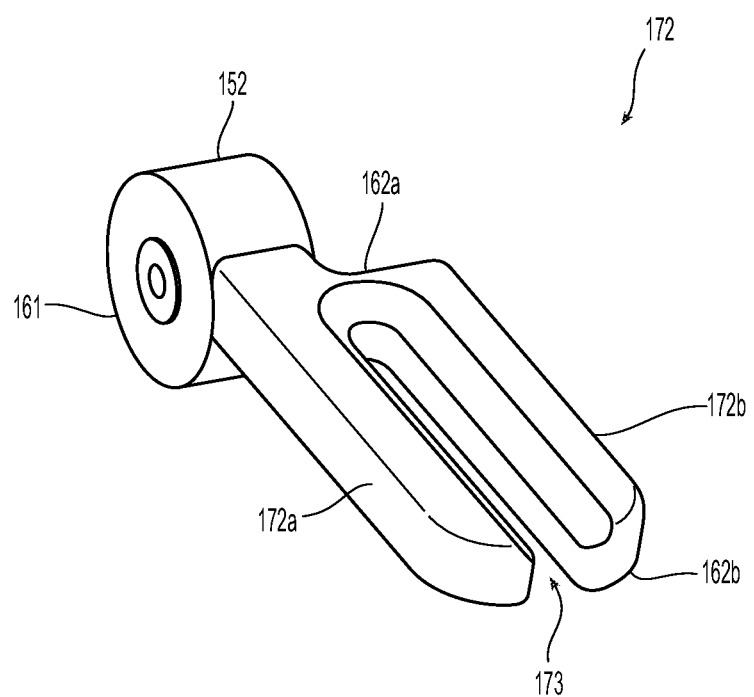
FIG. 3C is a perspective view of the upper jaw member in accordance with the present disclosure.

With reference now to FIGS. 3A-3C, jaw member 172 includes a longitudinal slot 173 defined therein thereby forming first and second grasping members 172a, 172b in a fork-like arrangement. Longitudinal slot 173 is configured to receive electrode 186 of jaw member 174, as will be described in more detail below. Jaw member 172 includes a jaw housing 195 having a grasping surface 194 (see FIG. 3B). Jaw housing 195 and/or grasping surface 194 may be formed from a high-strength, heat-resistant, and electrically insulative material, such as, without limitation, ceramic, zirconia, sialons, and the like. Grasping surface 194 may be smooth, serrated, or have opposing or interlocking teeth. In some embodiments, jaw housing 195 may be formed in full or in part from a metallic material. Grasping surface 194 is configured to face an opposing grasping surface 184 of jaw member 174 (FIGS. 2B and 2C) when jaw member 172 and jaw member 174 are assembled as jaw assembly 150.

A first and second sealing electrode 190a, 190b are disposed on the respective grasping surfaces 194 of first and second grasping members 172a, 172b (see FIG. 3B). In some embodiments, first and second electrodes 190a, 190b are embedded within grasping surface 194 such that the tissue-contacting surface of the first and second electrodes 190a, 190b are substantially flush with grasping surface 194 (e.g., within acceptable manufacturing tolerances for an electrosurgical jaw electrode, for example without limitation, +/-0.003"). In other embodiments, grasping surface 194 and/or first and/or second electrodes 190a, 190b may include one or more stop members (not shown) to maintain a predetermined minimum distance between jaw members 172, 174 when jaw members 172, 174 are in a closed position to effect a tissue seal. In some embodiments, first and/or second electrodes 190a, 190b may be recessed.

Sealing electrodes 190a, 190b are configured to conduct electrosurgical energy to or from tissue. In some embodiments, electrodes 190a, 190b are electrically independent and selectively configurable to deliver positive (+), negative (-), ground, and/or floating potential to tissue, depending upon the desired procedure being performed. In other embodiments, electrodes 190a, 190b are electrically coupled and configured to deliver a similar electrical signal to tissue. Sealing electrodes 190a, 190b are coupled to the electrosurgical generator 14 and/or controller 4 via one or more conductors and/or cables (not shown). It should be understood that sealing electrodes 190a, 190b may perform electrosurgical procedures or functions other than sealing, and may operate collectively or independently in a bipolar, monopolar, return electrode, ground electrode, passive electrode, or any other mode.

Figure 4A:
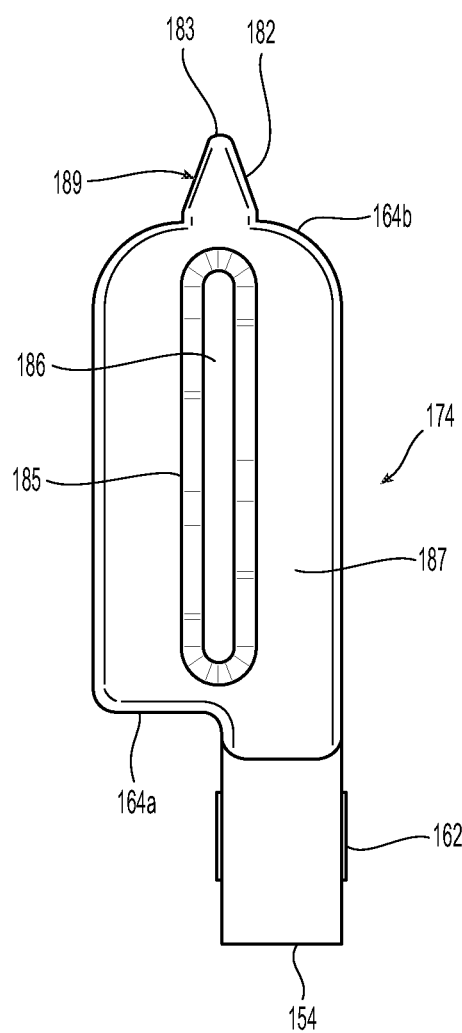
FIG. 4A is a view of the non-grasping side of the lower jaw member in accordance with the present disclosure.
Figure 4B:
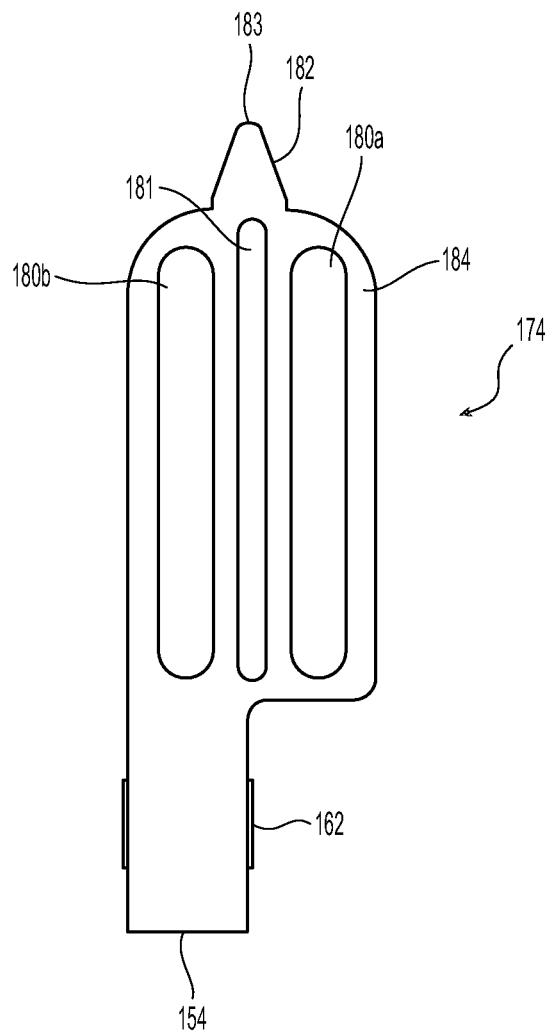
FIG. 4B is a view of the grasping side of the lower jaw member in accordance with the present disclosure.
Figure 4C:
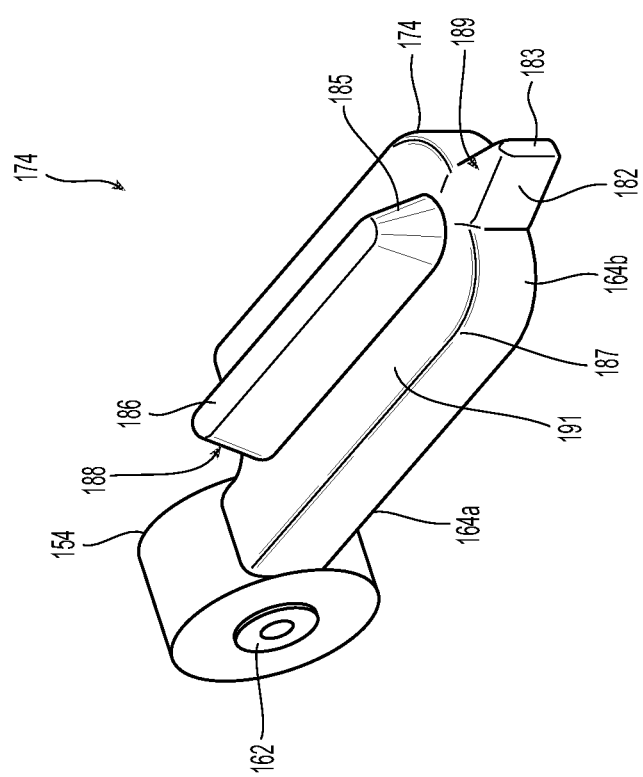
FIG. 4C is a perspective view of the lower jaw member in accordance with the present disclosure.

Turning to FIGS. 4A-4C, jaw member 174 includes a jaw housing 187 having a grasping surface 184 (FIG. 4B). Jaw housing 187 and/or grasping surface 184 may be formed from a high-strength, heat-resistant, and electrically insulative material, such as, without limitation, ceramic, zirconia, sialons, and the like. In some embodiments, jaw housing 187 may be formed in full or in part from a metallic material. As described above, grasping surface 184 faces the grasping surface 194 of jaw member 172.

Jaw member 174 includes a number of electrodes. First and second return electrodes 180a, 180b are longitudinally disposed on grasping surface 184 of jaw member 174, and a third return electrode 181 is longitudinally disposed centrally thereon, e.g., mid-way between first and second return electrodes 180a, 180b. As described with respect to sealing electrodes 190a, 190b of jaw member 172, in some embodiments, first, second, and third return electrodes 180a, 180b, and 181 are embedded within grasping surface 184 such that the tissue-contacting surface of first, second, and third return electrodes 180a, 180b, and 181 are substantially flush with grasping surface 184 while in yet other embodiments, first, second, and third return electrodes 180a, 180b, and 181 are disposed on grasping surface 184. Grasping surface 184 and/or first, second, and/or third return electrodes 180a, 180b, and 181 may include one or more stop members (not shown) to maintain a predetermined minimum distance between jaw members 172, 174, as previously described to effect a tissue seal.

Return electrodes 180a, 180b, and 181 are configured to conduct electrosurgical energy to or from tissue. In some embodiments, electrodes 180a, 180b, and 181 are electrically independent and selectively configurable to deliver positive (+), negative (-), ground, and/or floating potential to tissue, depending upon the desired procedure being performed. In other embodiments, electrodes 180a, 180b, and 181 are electrically coupled and configured to deliver a similar electrical signal to tissue. Electrodes 180a, 180b, and 181 are coupled to electrosurgical generator 14 and/or controller 4. It is to be understood that return electrodes 180a, 180b, and 181 may perform electrosurgical procedures or functions other than acting as a return electrode, and may operate collectively or independently in a bipolar, monopolar, sealing, ground electrode, passive electrode, or any other mode.

The central position of return electrode 181 of jaw member 174 corresponds to the longitudinal slot 173 when jaw member 172 and jaw member 174 oppose one another. In this manner, return electrode 181 is accessible, even if jaw members 172, 174 are in a closed position, to facilitate procedures performed in cooperation with another instrument, and, in particular, performed in cooperation with a second jaw assembly 150 under robotic control.

Figure 4D:
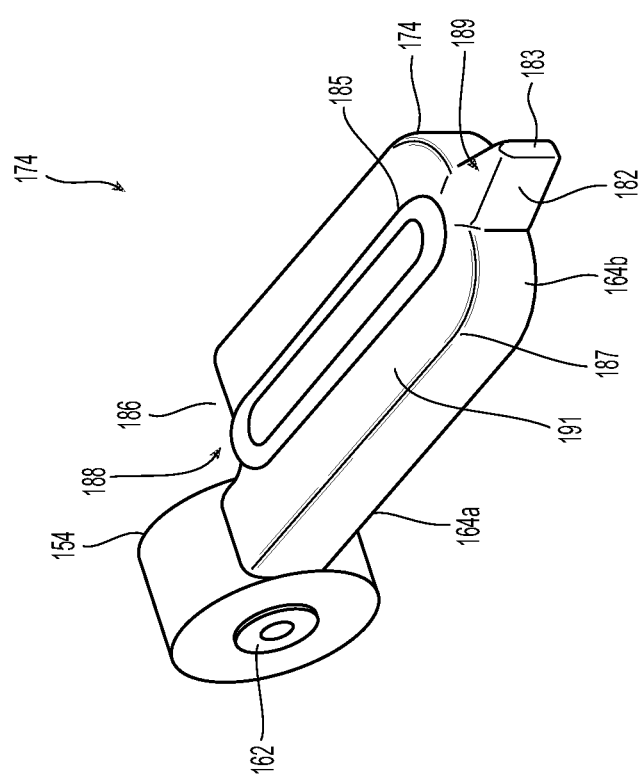
FIG. 4D is a perspective view of the lower jaw member showing a cutting electrode in a retracted position in accordance with the present disclosure.
Figure 5A:
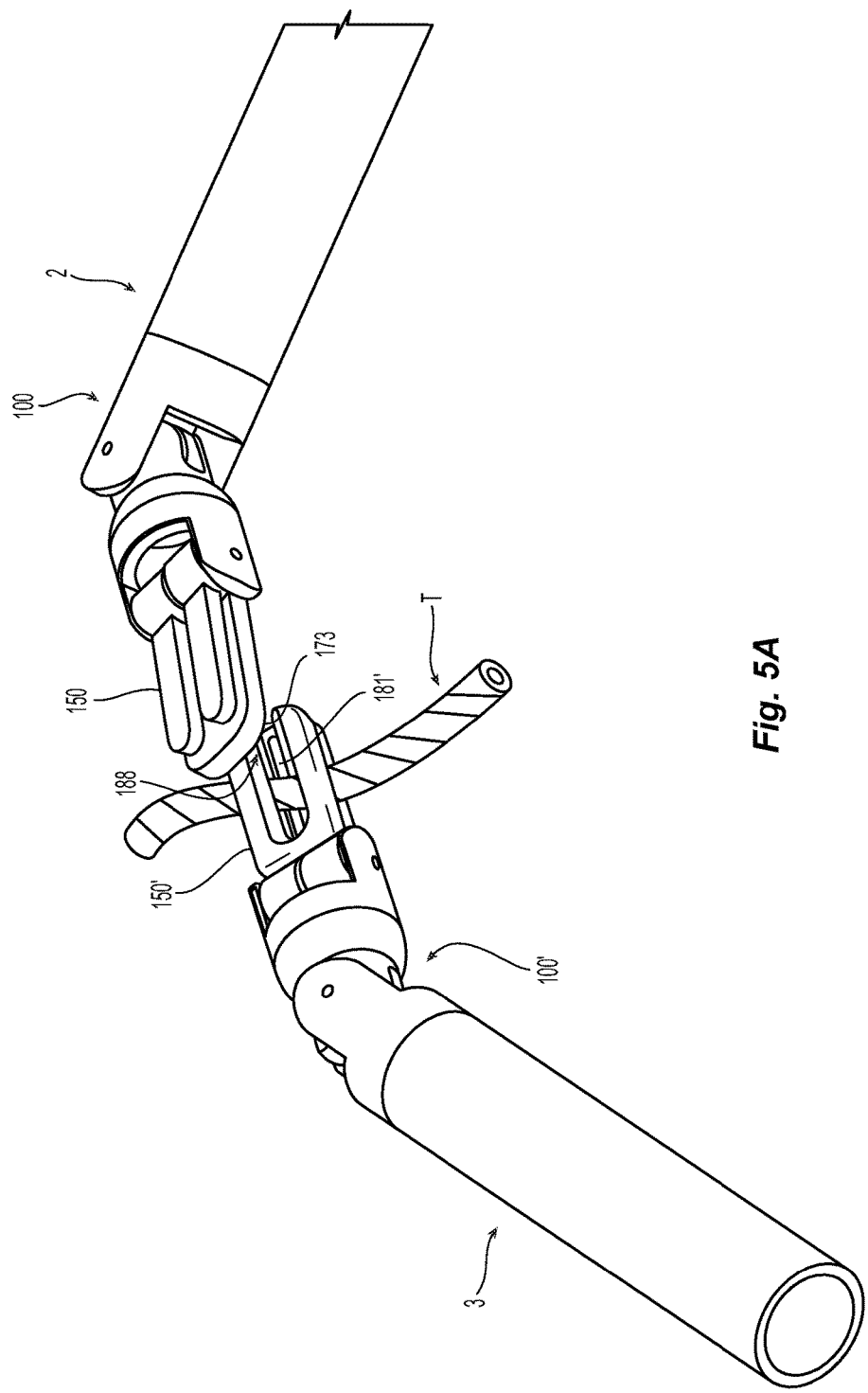
FIG. 5A illustrates two pair of end effectors cooperating to treat tissue in accordance with the present disclosure.
Figure 5B:
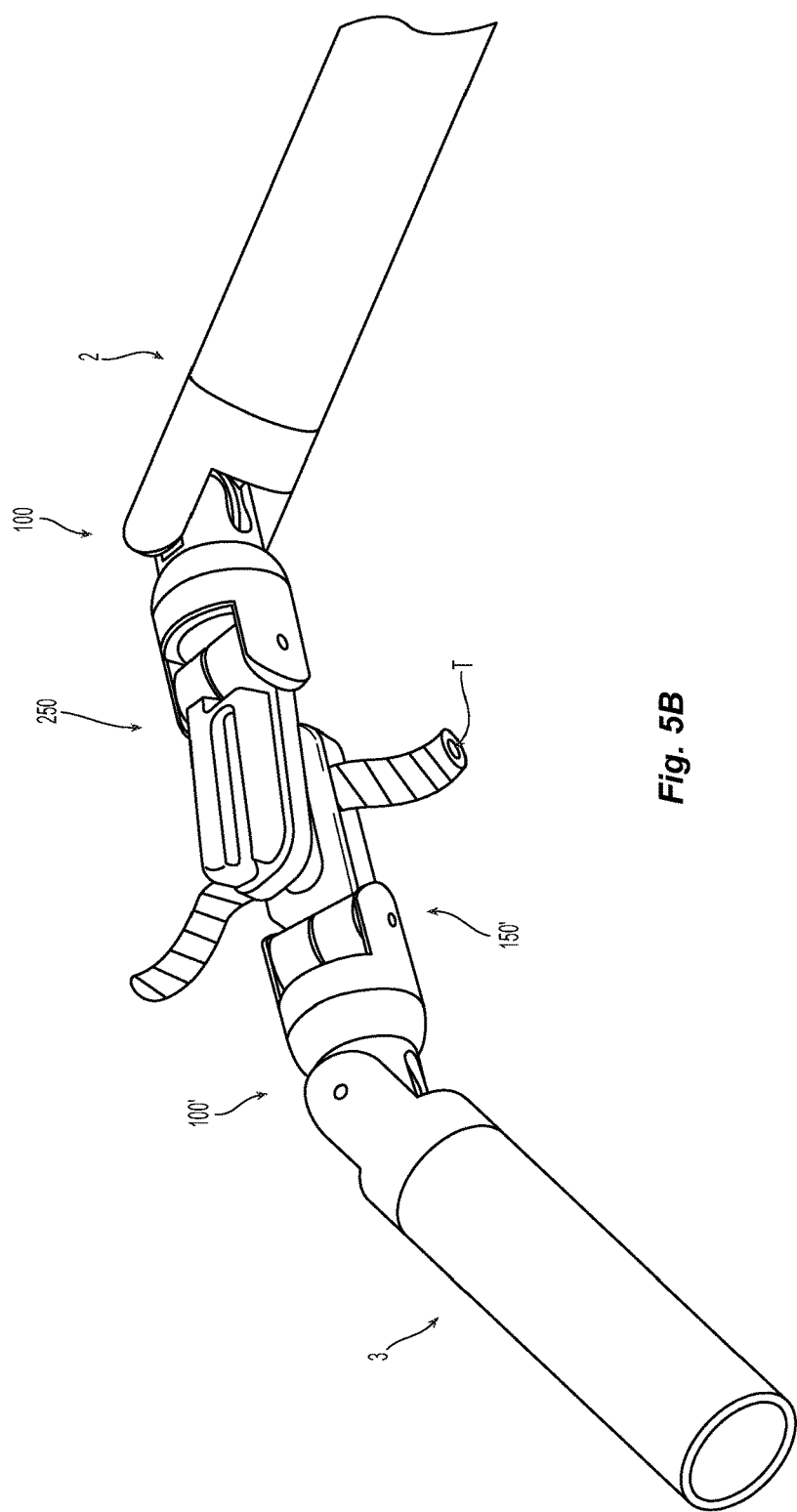
FIG. 5B illustrates another aspect of the two pair of end effectors cooperating to treat tissue.

In some embodiments, jaw member 174 includes a cutting electrode assembly 188 having a longitudinal electrode 186 that is positioned on a support ridge 185 disposed longitudinally on housing 187. Cutting electrode assembly 188 is configured such that the electrode assembly 188 of a first jaw assembly 150 may be operably received within the longitudinal slot 173 of a second jaw assembly 150' to deliver bipolar electrosurgical energy between the longitudinal electrode 186 of first jaw member 150 and third return electrode 181 of second jaw assembly 150' (FIGS. 5A and 5B). In embodiments, cutting electrode assembly 188 is movable between a raised position where electrode 186 is positioned above the surface of housing 187 and shown generally in FIG. 4C, and a lowered position where electrode 186 is positioned substantially flush with, or below, the surface of housing 187 (FIG. 4D). In the embodiment best shown in FIGS. 2C and 4C, electrode assembly 188 protrudes from a top surface 191 of housing 187, e.g., the opposite side of housing 187 from grasping surface 184.

Figure 4E:
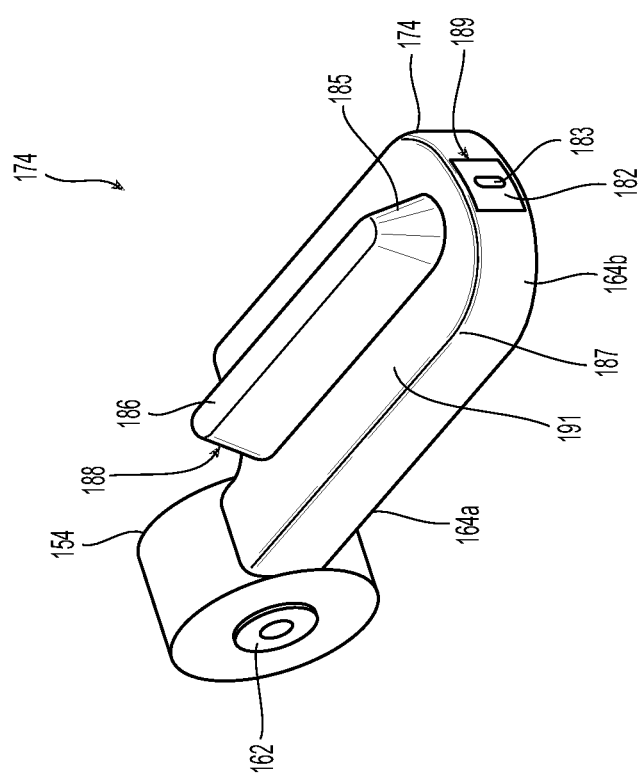
FIG. 4E is a perspective view of the lower jaw member a distal tip electrode in a retracted position in accordance with the present disclosure.

In some embodiments, jaw member 174 includes a tip electrode assembly 189 having a tip electrode 183 that is positioned on an electrode support 182. Electrode assembly 189 is configured to be operably received within the longitudinal slot 173 of a second jaw member 150' to deliver bipolar electrosurgical energy between tip electrode assembly 189 of first jaw assembly 150 and electrode 181 of second jaw assembly 150' (FIGS. 5A and 5B). In embodiments, tip electrode assembly 189 is movable between a first position where electrode 183 is positioned beyond a distal portion 164b of jaw housing 187 and shown generally in FIG. 4C, and a second position where electrode 183 is positioned closer to, substantially flush with, or below, a distal portion 164b of jaw housing 187 (FIG. 4E).

It should be understood that, while cutting electrode assembly 188 and tip electrode assembly 189 are configured to be operably received within the longitudinal slot 173, it is envisioned that cutting electrode assembly 188 and tip electrode assembly 189 may be used in conjunction with any other instrument and/or may be used to treat tissue in monopolar mode.

Turning now to FIGS. 5A and 5B, an example method of performing a robotic electrosurgical procedure on patient tissue T in accordance with the present disclosure is illustrated. First and second robotic arms 2, 3 having respective end effectors 100, 100' are utilized in the present example. As best seen in FIG. 5A, using any indicated interventional robotic surgical technique, end effector 100' is manipulated into a position whereby longitudinal slot 173' of jaw assembly 150' is positioned on one side of patient tissue T. End effector 100 is moved into position whereby cutting electrode assembly 188 of jaw assembly 150 is introduced into slot 173' of jaw assembly 150', thereby grasping patient tissue T therebetween. In some embodiments of the method, the motions positioning cutting electrode assembly 188' within slot 173 may be choreographed by control device 4. For example, a surgeon may position one or both end effectors 150, 150' such that the targeted patient tissue T is positioned loosely therebetween. After confirming that patient tissue T is positioned correctly, and that no undesired object is between the two jaw assemblies 150, 150', the surgeon may activate a "mating" function to complete the grasping operation. The mating function is executed by the robotic system, e.g., by control device 4, which, in turn, causes jaw assemblies 150 and 150' to draw together, thus clamping tissue T between electrode assembly 188 of jaw assembly 150, and return electrode 181' of jaw assembly 150'. Advantageously, the precise positioning capabilities of robotic arms 2, 3 enable accurate and repeatable control over tissue manipulation parameters during this phase of the procedure. For example, it may be desirable for a precise amount of tissue clamping force and/or a precise amount of tissue compression to be applied to tissue T. The gap distance between cutting electrode 186 and return electrode 181' may also be precisely controlled to effect a tissue seal. In general, when tissue cutting is desired, the amount of clamping force and/or tissue compression may be greater than when, for example, vessel sealing is desired (which typically calls for less clamping force and/or compression). In some embodiments, the mating function may accept one or more user inputs from the surgeon specifying the amount of clamping force and/or tissue compression to be applied. In some embodiments, the gap distance between opposing sealing surfaces during tissue treatment may range from about 0.001 inches to about 0.006 inches. In some embodiments, closure force on opposing sealing surfaces during tissue treatment is in the range of about 3 kg/cm$^2$ to about 16 kg/cm$^2$.

When tissue T is properly positioned and clamped between jaw assemblies 150, 150', electrosurgical energy is applied between cutting electrode 186 of jaw assembly 150, and return electrode 181' of jaw assembly 150', which, in turn, causes the desired electrosurgical effect to tissue T (e.g., cutting, sealing, coagulating, desiccating, etc.) In some embodiments, at least one of a tissue temperature, tissue impedance, tissue hydration, or other tissue property may be sensed and utilized to control the delivery of electrosurgical energy. After the delivery of electrosurgical energy is completed, end effectors 100, 100' are separated, thus releasing tissue T. In addition to the programmed control of mating, the application of electrosurgical energy and/or the release of tissue may be coordinated under control of control device 4.

Figure 6:
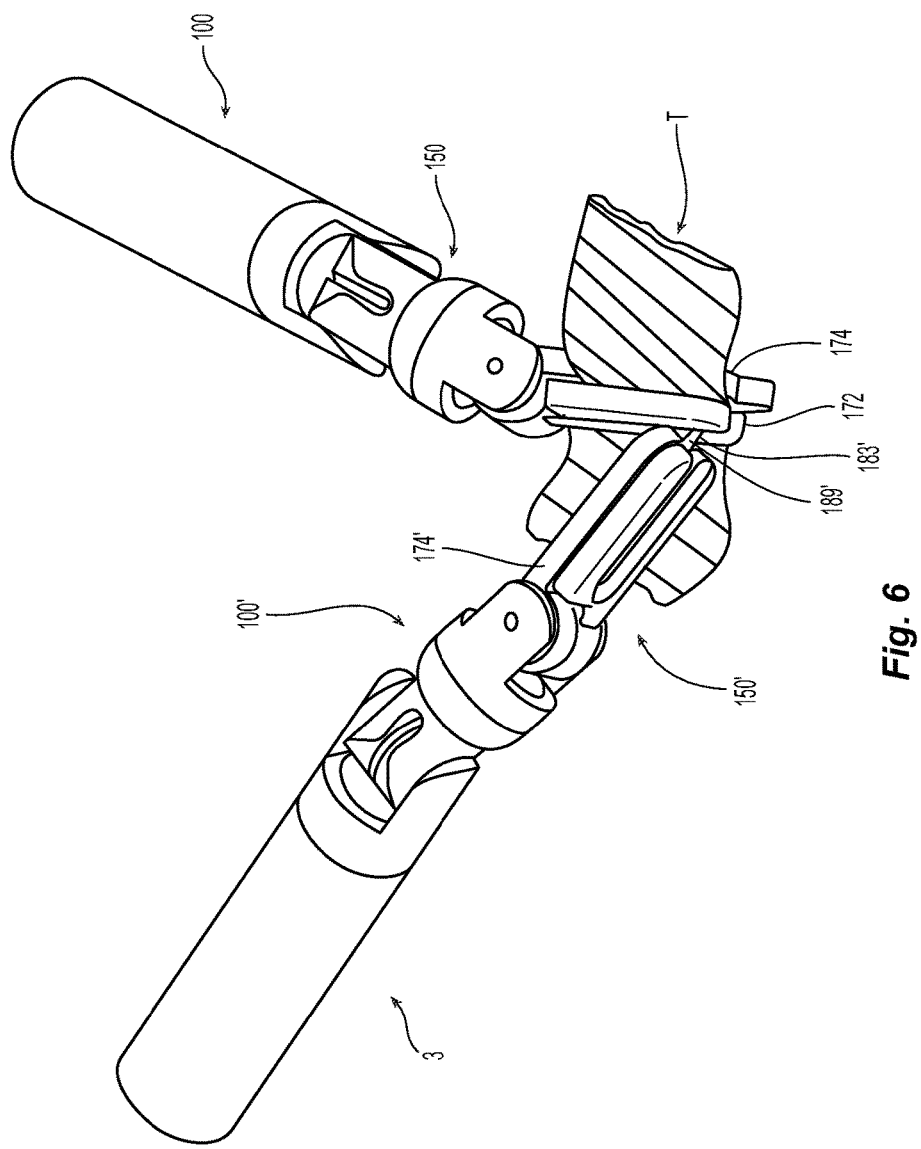
FIG. 6 illustrates a two pair of end effectors cooperating to treat tissue in accordance with another embodiment the present disclosure.

With reference now to FIG. 6, another example method of performing a robotic electrosurgical procedure in accordance with the present disclosure is illustrated. In the present example, end effector 100 is manipulated into position at the surgical site. Jaw members 172 and 174 of jaw assembly 150 are moved to an open position. The targeted tissue T is positioned between jaw members 172 and 174 of jaw assembly 150, and jaw members 174 and 172 are move to a closed position thereby grasping tissue T therebetween and exposing a strip of targeted tissue T within slot 173. A second end effector 100' is positioned at the surgical site and positioned such that tip electrode assembly 189' of jaw member 174' of jaw assembly 150' is introduced into slot 173 of jaw assembly 150. The introduction of tip electrode assembly 189' into slot 173 may be choreographed by control device 4, as described above, as may the clamping force and/or tissue compression between tip electrode 183' and return electrode 181.

When tissue T is properly positioned and tip electrode assembly 189' is introduced into slot 173, electrosurgical energy is applied between tip electrode 183' of jaw assembly 150', and return electrode 181 of jaw assembly 150. Concurrent with the application of electrosurgical energy, relative motion is imparted between jaw assembly 150 and jaw assembly 150' such that tip electrode 183' of jaw member 174' moves along the exposed tissue held within slot 173 of jaw assembly 150, which, in turn, causes the desired cutting, sealing, coagulating, desiccating, etc. to be performed to the exposed strip of targeted tissue T. After the delivery of electrosurgical energy is completed, end effectors 100, 100' are separated, and jaw members 172, 174 of jaw assembly 150 are moved to an open position, thus releasing tissue T. In embodiments any one, some, or all of the steps of grasping tissue T, positioning tip electrode assembly 189' within slot 173, the application of electrosurgical energy, moving tip electrode 183' within slot 173 to treat tissue, the separation of end effectors 100, 100' and/or the opening of jaw members 172, 184 release of tissue may be coordinated by control device 4.

Figure 7:
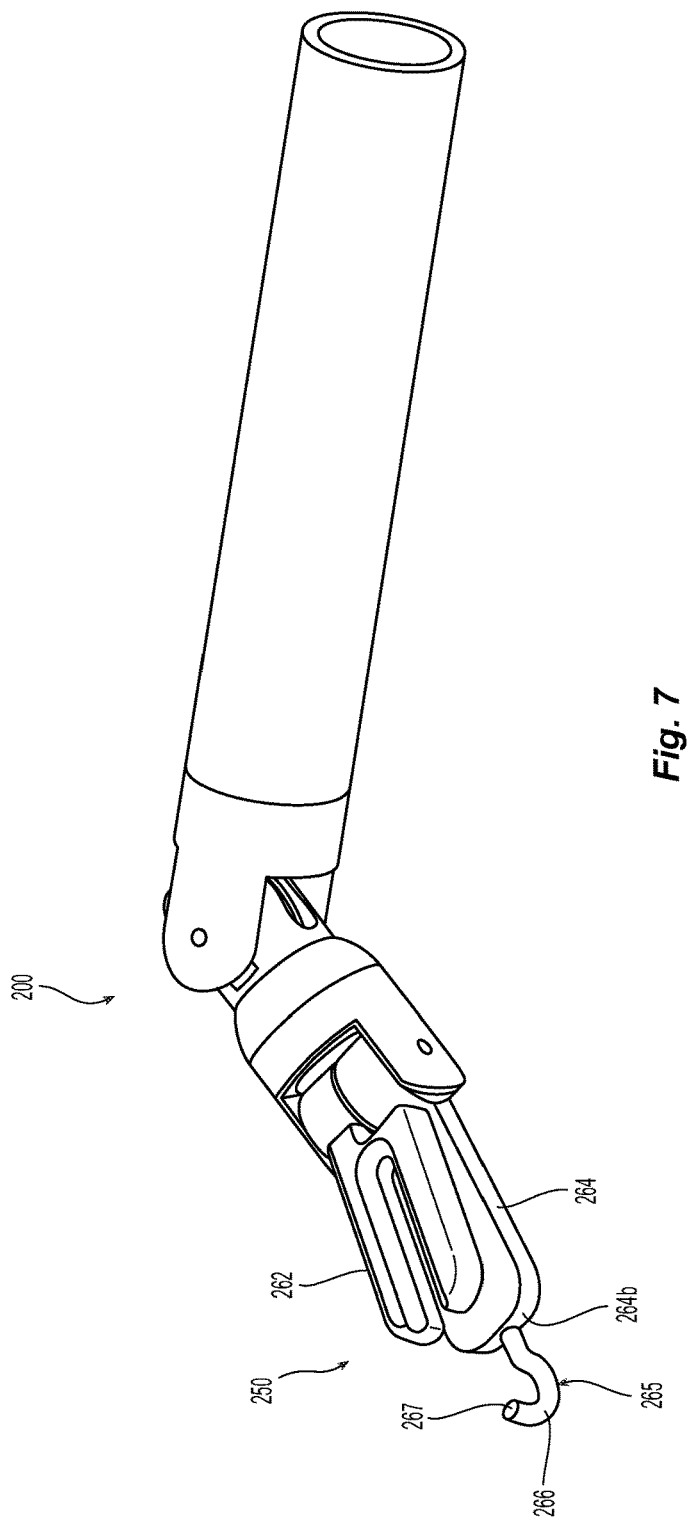
FIG. 7 illustrates another embodiment of the end effector of the present disclosure for use with the medical workstation of FIG. 1, illustrating a jaw assembly having a tissue manipulation feature.

In yet another example embodiment best illustrated in FIG. 7, an end effector 200 includes a jaw assembly 250 having a first jaw member 262 and a second jaw member 264. First and second jaw members 262, 264 include similar features to jaw members 172, 174 as described hereinabove. In the present embodiment, jaw member 264 includes a hook electrode assembly 265 disposed at a distal end 264b thereof. Hook electrode assembly 265 includes a body electrode 266 and an end electrode 267. In some embodiments, body electrode 266 and end electrode 267 are electrically independent and selectively configurable to deliver positive (+), negative (−), ground, and/or floating potential to tissue, depending upon the desired procedure being performed. In other embodiments, body electrode 266 and end electrode 267 are electrically coupled and configured to deliver a similar electrical signal to tissue. Body electrode 266 and end electrode 267 are coupled to electrosurgical generator 14 and/or controller 4. During use, hook electrode assembly 265 may be employed using any of the cooperative "two handed" electrosurgical techniques described herein, may be utilized to perform conventional electrosurgical procedures, and/or may be used for non-electrosurgical manipulation of tissue. Other forms of distal electrode assemblies are contemplated within the scope of the present disclosure, including without limitation, a scalpel, a spatula, a scissors, a needle, a probe, and/or a sensing device.

The described example embodiments of the present disclosure are intended to be illustrative rather than limiting, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law.

What is claimed is:

1. A robotic surgical system for performing electrosurgical procedures, comprising:
   a first end effector operably coupled to a first robot arm, comprising:
      a first jaw member including:
         a jaw housing;
         a longitudinal slot defined in the jaw housing of the first jaw member forming first and second grasping members, each of the first and second grasping members having a grasping surface configured to face an opposing grasping surface of a second jaw member;
         a first sealing electrode disposed on the first grasping surface; and
         a second sealing electrode disposed on the second grasping surface; and
      the second jaw member including:
         a housing;
         the opposing grasping surface included on the housing of the second jaw member and configured to face the first and second grasping surfaces of the first jaw member;
         first and second return electrodes longitudinally disposed on the opposing grasping surface of the second jaw member, wherein the first and second return electrodes are configured to oppose the first and second sealing electrodes of the first jaw member;
         a third return electrode longitudinally disposed on the opposing grasping surface of the second jaw member centrally between first and second return electrodes, wherein the third return electrode is configured to oppose the longitudinal slot of the first jaw member; and
         a cutting electrode; and
   a second end effector operably coupled to a second robot arm, the second end effector defining a longitudinal slot and including a return electrode;
   an electrosurgical generator in operable communication with the first and second end effectors, the electrosurgical generator configured to selectively deliver electrosurgical energy; and
   a control device configured to manipulate the first and second end effectors according to a user input and a preprogrammed sequence of actions, wherein the preprogrammed sequence of actions includes:
      introducing the cutting electrode of the first end effector into the longitudinal slot of the second end effector to grasp tissue therebetween;
      delivering the electrosurgical energy between the cutting electrode of the first end effector and the return electrode of the second end effector to treat the tissue grasped therebetween; and
      withdrawing the cutting electrode of the first end effector from the longitudinal slot of the second end effector.

2. A robotic surgical system for performing electrosurgical procedures, comprising:
   a first end effector operably coupled to a first robot arm, comprising:
      a first jaw member including:
         a jaw housing;
         a longitudinal slot defined in the jaw housing of the first jaw member forming first and second grasping members, each of the first and second grasping members having a grasping surface configured to face an opposing grasping surface of a second jaw member;
         a first sealing electrode disposed on the first grasping surface; and
         a second sealing electrode disposed on the second grasping surface; and
      the second jaw member including:
         a housing;
         the opposing grasping surface included on the housing of the second jaw member and configured to face the first and second grasping surfaces of the first jaw member;

first and second return electrodes longitudinally disposed on the opposing grasping surface of the second jaw member, wherein the first and second return electrodes are configured to oppose the first and second sealing electrodes of the first jaw member;

a third return electrode longitudinally disposed on the opposing grasping surface of the second jaw member centrally between first and second return electrodes, wherein the third return electrode is configured to oppose the longitudinal slot of the first jaw member;

a tip electrode; and a cutting electrode;

a second end effector operably coupled to a second robot arm, the second end effector defining a longitudinal slot and including a third return electrode;

an electrosurgical generator in operable communication with the first and second end effectors; and a control device configured to manipulate the first and second end effectors according to a user input and a preprogrammed sequence of actions, wherein the preprogrammed sequence of actions includes:

introducing the tip electrode of the first end effector into a first end of the longitudinal slot of the second end effector;

delivering the electrosurgical energy between the tip electrode of the first end effector and the third return electrode of the second end effector to treat tissue;

moving the tip electrode of the first end effector along the longitudinal slot of the second end effector toward a second end of the longitudinal slot of the second end effector to treat the tissue; and withdrawing the tip electrode of the first end effector from the longitudinal slot of the second end effector.

* * * * *